United States Patent [19]

Archer et al.

[11] Patent Number: 5,638,657

[45] Date of Patent: Jun. 17, 1997

[54] SYSTEM AND METHOD FOR AUTOMATICALLY FEEDING, INSPECTING AND DIVERTING TABLETS FOR CONTINUOUS FILLING OF TABLET CONTAINERS

[75] Inventors: John R. Archer, Herts; David E. Cumpstey; Richard H. Gray, both of Cambridge; Stephen Owen, Herts, all of United Kingdom

[73] Assignee: Merck & Co., Inc., Rahway, N.J.

[21] Appl. No.: 609,406

[22] Filed: Mar. 1, 1996

Related U.S. Application Data

[62] Division of Ser. No. 239,794, May 9, 1994, Pat. No. 5,522,512.

[51] Int. Cl.$^6$ .............................. B65B 1/06; B65B 39/00; B65B 43/50
[52] U.S. Cl. .............................. 53/253; 53/244; 53/249
[58] Field of Search .............................. 53/249, 250, 253, 53/244, 240, 237, 272

[56] References Cited

U.S. PATENT DOCUMENTS

| | | | |
|---|---|---|---|
| 2,587,686 | 3/1952 | Berry | 209/81 |
| 2,700,496 | 1/1955 | Dickey et al. | 53/253 X |
| 3,040,887 | 6/1962 | Cornelison | 209/82 |
| 3,123,217 | 3/1964 | McMillan et al. | 209/920 X |
| 3,283,475 | 11/1966 | Pinto | 53/253 X |
| 3,283,896 | 11/1966 | Jirik et al. | 209/111.6 |
| 3,505,777 | 4/1970 | Tsutsumi | 53/253 X |
| 3,664,084 | 5/1972 | Meckley | 53/253 X |
| 4,168,005 | 9/1979 | Sandbank | 209/552 |
| 4,231,478 | 11/1980 | Stone | 209/576 |
| 4,235,067 | 11/1980 | Parsons | 53/253 X |
| 4,324,336 | 4/1982 | Sandbank | 209/589 |
| 4,369,886 | 1/1983 | Lane et al. | 209/580 X |
| 4,901,841 | 2/1990 | Haggerty et al. | 209/920 X |
| 4,909,373 | 3/1990 | Geerts | 198/365 |
| 5,135,113 | 8/1992 | Mayer et al. | 209/539 |
| 5,135,114 | 8/1992 | Satake et al. | 209/920 X |
| 5,191,741 | 3/1993 | Jones | 53/475 |
| 5,238,124 | 8/1993 | Cane et al. | 209/660 |

*Primary Examiner*—James F. Coan
*Attorney, Agent, or Firm*—Francis P. Bigley; Elliott Korsen; Mark R. Daniel

[57] ABSTRACT

A system and method for automatically feeding, inspecting and diverting tablets for continuous filling of tablet containers includes a tablet conveyor system which divides the tablets in a plurality of tablet streams for inspection by color, size and shape. Following the tablet inspection, each tablet passes through a tablet diverter which diverts the tablets to a recycle stream, reject stream or one of two bottle filling positions based upon instruction from the inspection. A bottle conveyor system is provided which feeds empty bottles into a bottle escapement mechanism which positions the empty bottles for filling. Filled bottles are moved from the bottle escapement mechanism to an exit conveyor. The entire system is computer controlled by various control mechanisms to enable the system to be fully operational without operator assistance.

7 Claims, 10 Drawing Sheets

SYSTEM AND METHOD FOR AUTOMATICALLY FEEDING, INSPECTING AND DIVERTING TABLETS FOR CONTINUOUS FILLING OF TABLET CONTAINERS

This is a division of application Ser. No. 08/239,794, filed May 9, 1994, now U.S. Pat. No. 5,522,512.

FIELD OF THE INVENTION

The present invention is directed to a system and method for automatically feeding, inspecting and diverting tablets for continuous filling of tablet containers and, in particular, a system and method which is capable of sorting a continuous stream of tablets to automatically fill a container with a predetermined number of tablets such as prescription pills, for direct distribution. In the case of pharmaceuticals, the filled container is suitable for distribution to the user or wholesaler.

BACKGROUND OF THE INVENTION

In the prior art, various methods and apparatus have been proposed to inspect a continuous stream of moving articles and divert unacceptable articles from the moving stream. U.S. Pat. No. 3,283,896 to Jirik et al. discloses a coffee bean sorting apparatus which uses lamps to inspect a continuous stream of coffee beans to sort undesirable coffee beans and debris from desirable coffee beans. A deflector arm directs the coffee beans into the appropriate bin based upon the inspection system.

U.S. Pat. Nos. 4,168,005 and 4,324,336 to Sandbank disclose a separating apparatus which utilizes a conveyor belt, inspection system and diverter valve to separate a continuous stream of traveling articles such as crops, clods of earth or the like.

Apparatus have also been proposed for sorting tablets or capsules. U.S. Pat. No. 5,238,124 to Cane et al. discloses an apparatus utilizing rotating combs to separate a continuous stream of traveling capsules based upon the capsule configuration.

U.S. Pat. No. 5,135,113 to Mayer et al. discloses a high-speed tablet sorting machine which utilizes capacitive measurement to determine tablet weight. Depending on the sensed capacitive measurement, the tablets are diverted into one of two paths to an appropriate collection bin.

U.S. Pat. No. 5,191,741 to Jones discloses a fluidized bed bottle filling system. In this system, tablets are transferred from bulk into small containers such as bottles. Typically, the filling system includes a moving bin made of a series of grooved slats which pass beneath a quantity of fluidized tablets. The grooves are further subdivided into cavities and one tablet is permitted to drop into each cavity until all of the cavities are filled. After the filled slats move from beneath the tablet bin, the tablets are ejected, collated and fed into each bottle via transport through a manifold system.

Although prior art systems have been proposed to automatically fill tablet containers, many containers are still manually filled at the pharmacy level based upon a given prescription. While this method of filling may provide an accurate and high quality prescription drug filled container, it is tedious, time consuming and expensive.

Automatic systems such as the fluidized bed bottle filling system of Jones provide advantages in the time taken to fill a given container but are deficient in the ability to provide a filled container that consistently contains the correct number and type of tablets for use by a consumer.

In view of these deficiencies, a need has developed to provide an automatic system which continuously fills tablet containers and is capable of feeding, inspecting and diverting tablets based upon a predetermined set of parameters to provide a tablet container having the proper number and type of tablets therein.

In response to this need, the present invention provides a system and method for automatically feeding, inspecting and diverting tablets for continuous filling of tablet containers. In this manner, a prescription can be automatically filled using the inventive system and method and mailed or given to a user without the need for a pharmacist.

SUMMARY OF THE INVENTION

It is a first object of the present invention to provide a system and method which automatically and continuously fills tablet containers for direct distribution to a user.

It is another object of the present invention to provide a system and method which automatically feeds, inspects and diverts tablets during the filling operation to assure that the filled containers have the proper number and type of tablet therein.

Another object of the present invention is to provide a system and method which can inspect every tablet for size, shape and color, has no mechanical parts specific to a particular tablet, so it can handle any tablet shape.

A further object is for a system which can operate at high speed and include rapid changeover capability, by virtue of its use of belts rather than tablet-specific tooling.

It is a further object of the present invention to provide a system and method which provides enhanced assurance of product quality, reduced operating, maintenance, and manpower needs and the ability to produce smaller economic lot sizes which reduce product inventories and increase responsiveness to filled container requirements.

It is another object of the present invention to provide a system and method which offers a simple mechanical configuration coupled to sensing and control features which allow automatic calibration and self learning of new tablet sizes, is easily accessible for cleaning and periodic maintenance, permits continuing operation in the event of a partial interruption in tablet flow, has the ability to accommodate different bottle shapes and eliminates direct operator involvement during normal operation.

A still further object of the present invention is to provide a bottle or container filling system which permits continuous filling of a continuous stream of discrete bottles with a continuous stream of articles such as tablets for pharmaceutical use, vitamins or any material typically contained in bottles or containers.

Other objects and advantages of the present invention will become apparent as a description thereof proceeds.

In satisfaction of the foregoing objects and advantages, the present invention comprises a system for automatically filling bottles with tablets comprising a hopper for storing tablets, a feeder for diverting the stored tablets into a plurality of tablet streams, and a conveyor for continuously conveying the plurality of tablet streams from the feeder past an inspection station. The inspection station comprises a means for inspecting each tablet passing the inspection station by color, shape and size (area) and producing a first signal indicating whether each tablet satisfies predetermined target values, as well as counting each tablet. A tablet diverter receives the tablets passing the inspection system, the tablet diverter including flap valves wherein the flaps divert the tablet into a stream for recycling, rejection, or bottle filling. Each flap is responsive to the first signal from the inspection station for diverting a tablet to a given stream. A bottle filling station receives tablets satisfying predetermined target values via the bottle filling stream. The bottle filling station includes a bottle escapement device which positions at least a pair of empty bottles for filling, an in-feed bottle conveyor feeding a stream of empty bottles to the bottle escapement device and an out-feed bottle conveyor receiving filled bottles from said bottle escapement device and directing the stream of filled bottles away for further processing such as capping, labeling, shipping or the like. A controller regulates the feeder, the inspection station and the tablet diverter such that tablets can be fed automatically from the hopper to said inspection system, inspected and diverted into one of the recycle, reject or bottle filling streams. The controller further regulates the bottle filling system such that empty bottles can be continuously filled by tablets diverted to said bottle filling stream.

In another aspect of the invention, a method of automatically filling bottles with tablets comprises the steps of providing a source of tablets, separating the source of tablets into a plurality of tablet streams, feeding the plurality of tablet streams such that each tablet stream comprises a continuous stream of discrete tablets. Each discrete tablet is inspected for at least one of size, color and shape. The inspected tablets are diverted based on the inspection step into a recycle stream, reject stream or accept stream. A continuous stream of empty bottles is provided wherein at least one empty bottle is positioned to receive diverted tablets from the accept stream to fill the empty bottle. The filled bottle is recovered for further processing such as capping, labeling, shipping or the like. The separating, feeding, inspecting, diverting, providing, positioning and recovering steps are controlled to automatically fill the empty bottles with a predetermined number and type of tablet.

In yet another aspect of the invention, a device is provided for filling individual containers traveling in a continuously moving stream with a continuous stream of discrete items. The device includes a body having a first opening, a first recess sized to receive the individual containers and a first chute interconnecting the first opening and the first recess. The body also includes a second opening, a second recess sized to receive an individual container and a second chute interconnecting the second opening and second recess. Means are provided on the body for connecting the body to a drive which can rotate the body in 180° segments. The first recess and second recess are located on the body on a line that intersects a longitudinal axis thereof. The first and second openings are sized and the first and second chutes are configured to receive the continuous stream of discrete items while the body is rotated in a 180° segment so that an individual container, in either the first or second recess, can be continually filled with discrete items traveling through either the first or second chute during body rotation.

Preferably, the body is cylindrical in shape with the first and second recesses diametrically opposed in the cylindrical body side surface. In this embodiment, the bottom of the body can be configured to receive the drive for rotating the body with the top of the body having the first and second openings therein.

More preferably, one of the openings is aligned with a longitudinal axis of the body with the other opening at least partially surrounding the opening located on the longitudinal axis.

In a preferred embodiment, the device can be used to fill individual containers with tablets for prescription use. However, the device can be used for any continuous stream of discrete items that can be diverted between the first and second openings for sequentially filling a plurality of individual containers in a continuous fashion.

BRIEF DESCRIPTION OF THE DRAWINGS

Reference is now made to the drawings accompanying the invention wherein.

DESCRIPTION OF THE PREFERRED EMBODIMENTS

The inventive system and method is directed to an automatic tablet filling system which enhances product quality and provides for efficient small lot-sized packaging. Using a simple mechanical configuration and sophisticated sensing and control, tablets can be fed from a hopper using vibratory feeders through an inspection system. Once inspected, the tablets can be sorted for recycle, rejection or bottle filling.

The inventive system and apparatus offer advantages over other prior an designs in the ability to accommodate different tablet types and bottle sizes without a need for changes in system set up. Other features include automatic calibration and self learning of new tablet types, elimination of direct operator involvement during normal operation and the ability to continue bottle filling in the event of one or more tablet streams becoming unavailable.

These features result in enhanced assurance of product quality, fast batch to batch changeovers and reduced operating costs, maintenance and manpower needs. In addition, packaging line efficiency and utilization is increased and smaller economic lot sizes are obtainable which reduces product inventories and increases responsiveness.

The inventive system and method make it possible to fill bottles with a predetermined number and type of tablets.

Although it is anticipated that the system can handle a wide range of tablet sizes, preferred tablet dimensions are as follows (These are based on circle diameters):

Maximum tablet dimension—0.8" or 20 mm

Minimum tablet dimension—0.2" or 5 mm

Minimum tablet thickness—0.1" or 2.5 mm

Likewise, any size bottle is believed to be adaptable with the present system. Preferably, 30, 75 and 120 ml bottles are used, but bottles as large as 250 or even 500 ml can be employed.

Figure 1:
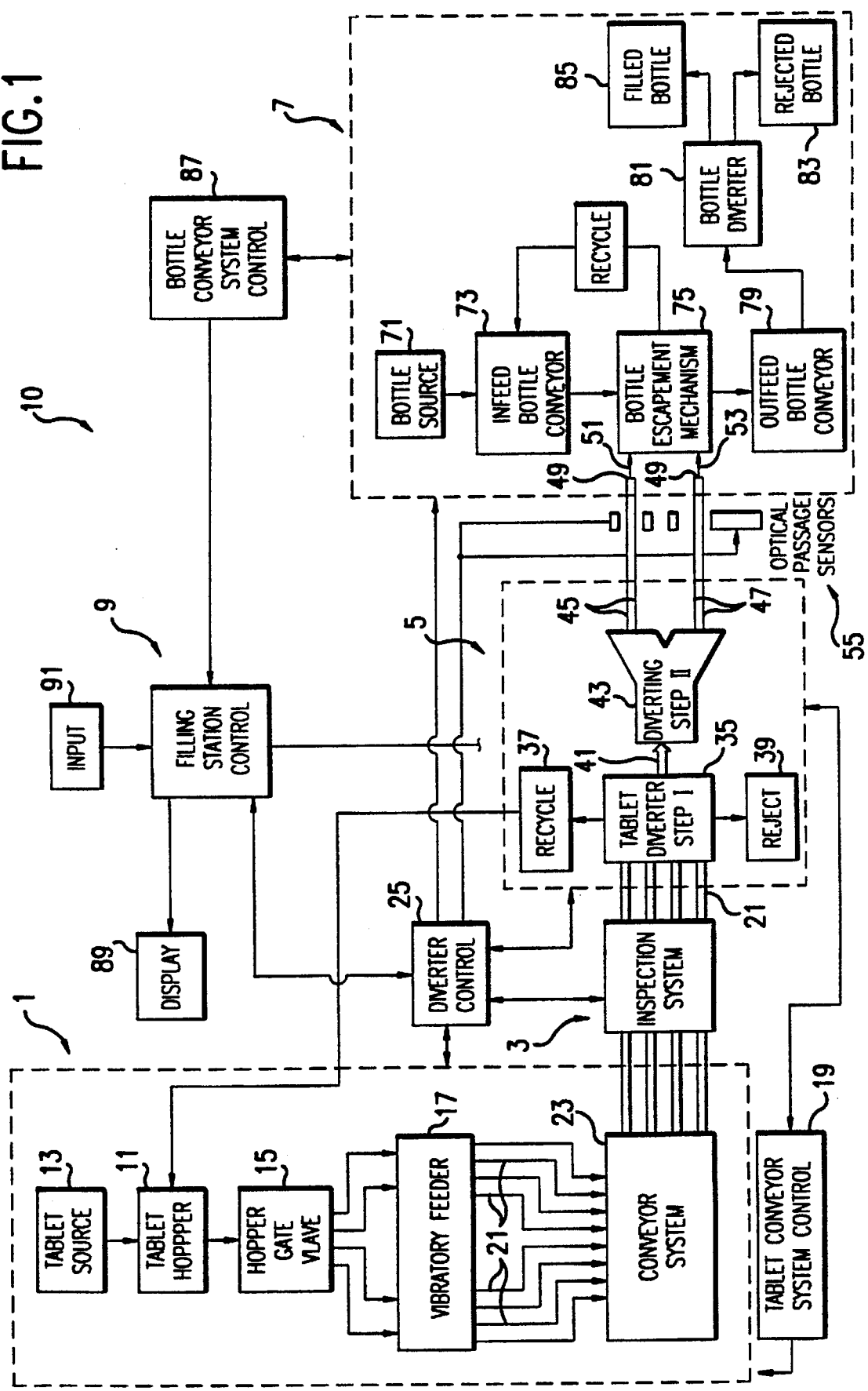
FIG. 1 is schematic diagram showing the system components.

With reference now to FIG. 1, the inventive system is generally designated by the reference numeral 10 and comprises a tablet conveyor system 1, and inspection system 3, a tablet diverter system 5, a bottle conveyor system 7 and a filling station control 9. The tablet conveyor system 1, tablet diverter system 5 and bottle conveyor system 7 are identified by the hatched rectangular areas. Each of the above-listed systems and control will be described hereinafter under separate headings.

Tablet Conveyor System

The tablet conveyor system 1 includes a tablet hopper 11 which can be filled using any conventional tablet source 13. The tablet hopper 11 is stainless steel and can be mounted onto a stainless framework using a pivot, which enables the hopper to be pivoted from the vertical to the horizontal for easy cleaning.

The tablet hopper 11 is used to feed a vibratory feeder 17 through four separate discharge ports of chutes (not shown) from the hopper gate valve 15.

The hopper can have two low level sensors to signal when it should be filled and two high level sensors to signal when to stop filling. The sensors are preferably a capacitive type with a plug at the sensor for removal if required. The hopper capacity is variable depending on its size but is preferably approximately 80 liters.

The vibratory feeder 17 produces well defined and singulated streams of tablets 21 (two for each of the four channels emanating from the hopper gate valve 15). Although any feeder can be used to accomplish this function, a vibratory feeder is preferred. The feeder 17 can be a stainless steel type which is mounted onto a frame using rubber anti-vibration mounts. A vibratory drive, fully enclosed, can be underslung beneath a vibratory trackway of the feeder. The vibratory trackway linear speed can be varied automatically for different tablets by adjusting the vibration amplitude of the vibratory drive. Optionally, a sift mesh can be provided on the vibratory feeder which enables small tablet fragments and/or dust to drop into a collection bin or vacuum extractor.

The four pairs of tablet streams 21 are fed to a conveyor system 23. The conveyor system transports each of the eight streams of tablets to an inspection system 3 for sorting prior to bottle filling.

In a preferred embodiment, the conveyor system can be mounted on a framework and can include up to 4 separate or 2 paired FDA acceptable belts, of suitable width. Seamless black PVC belts, 300 mm wide, with an FDA approved clear PVC overlay are exemplary. Easy belt changing is desirable to facilitate easy cleaning. Each belt can be kept separate by a barrier system, so that each line can package a different tablet. Typically, the belt will run at a speed of 200 mm/sec. but other speeds may be used depending on system variables.

The seamless black belts can run over a bed plate which extends beyond the outer belt edges with its sides being turned to minimize the possibility of tablet entrapment.

Preferably, the belt conveyor can include a rolling knife edge assembly to control the tablet exit trajectory as the tablets leave the belt, a belt tensioner mechanism and a belt cleaning mechanism to assure that the belt is clean when receiving tablets. The cleaning mechanism can be any known type, for example, a cloth or a vacuum system.

By providing a plurality of separate individual belts or pairs of belts, increased flexibility and production is achieved since each belt can be serviced independently of other belts in operation.

Inspection System

Inspection system 3 is part of the quality control aspect of the tablet bottle filling system 10. Each system inspects two parallel streams of tablets as they pass on the belt to check that the tablets are of the correct color, shape and size and are undamaged. Damage as well as size is checked to assure efficacy of dose; about 10% of the tablet can be missing before rejecting one tablet. As shown in FIG. 1, one inspection system 3 is provided for each pair of parallel streams of tablets 21. In total, for the four pairs of parallel streams, four inspection systems are provided.

Once an individual tablet has been inspected by the system 3, the result of the inspection is sent to the diverter control 25 which, in turn, utilizes this information to control the tablet diverter system 5 for filling bottles.

Figure 2:
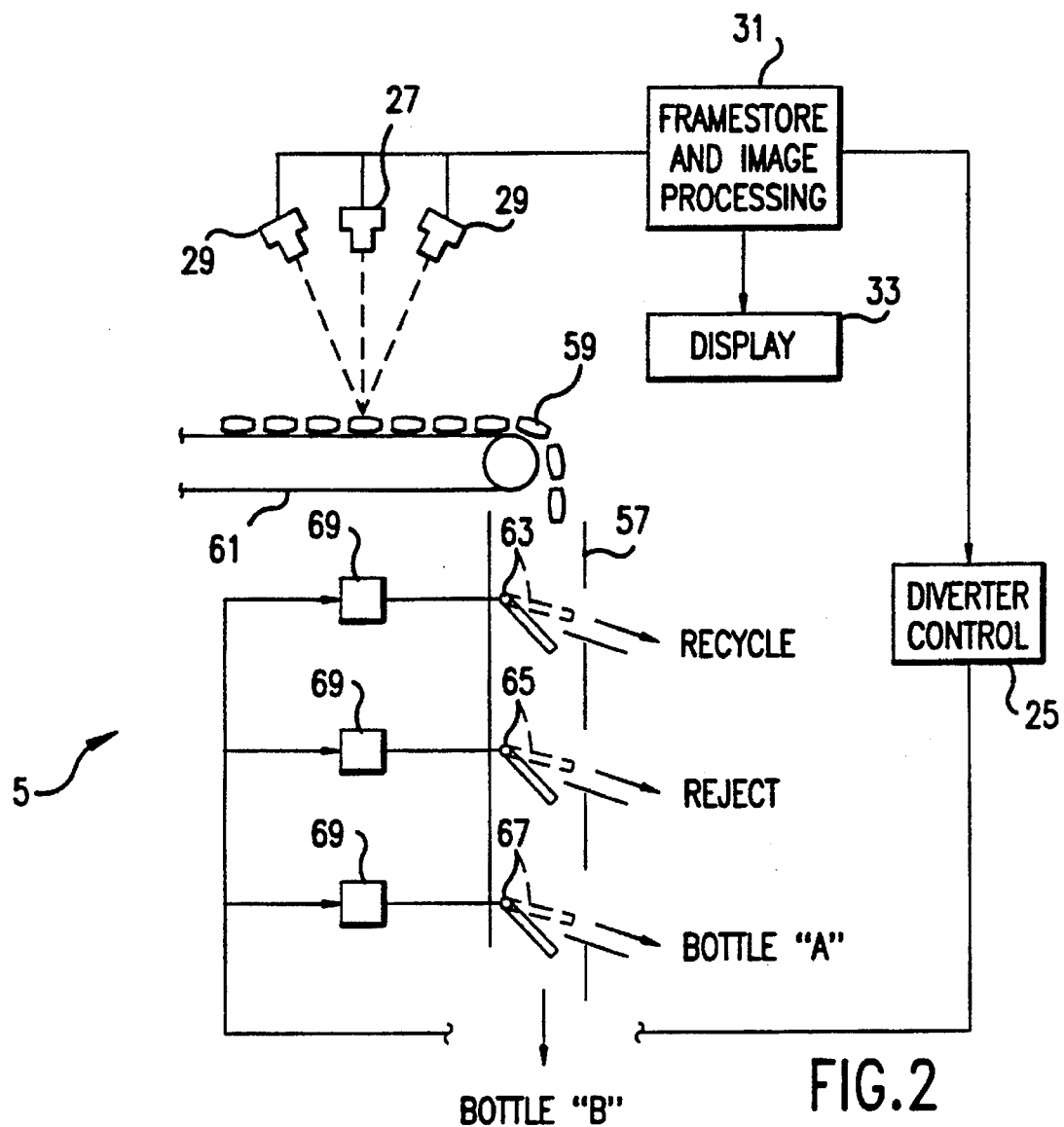
FIG. 2 is a schematic representation representing an inspection of one stream of traveling tablets in the inventive system.

FIG. 2 details inspection system components. The system uses three line scan cameras: one camera 27 to provide data on shape and area and one color data. This camera also judges damage. The other two cameras 29 provide data on the other two colors. The cameras are connected to a framestore and image pre-processing hardware 31 which extracts edge and color information from the scanline date. The framestores include interfaces to allow a monitor 33 to be connected to observe the image. The data from the image pre-processing hardware is passed to a digital signal processor via a first in first out buffer, and an associated interrupt is generated at the end of each scanline. The interrupt will be discussed in greater detail hereinafter. The digital signal processor sub-system consists of a processor, data memory, program data memory and non volatile memory. The code for the inspection system is stored in the non-volatile memory and is loaded into fast program memory on initialization. Once the sensed data has been processed by the digital signal processor, the results are sent to the diverter control 25 via the communication first in first out buffers for tablet diversion.

To achieve the color sensitivity necessary to resolve the differences between similar tablet shades it is necessary to have tightly defined color channels and carefully controlled illumination. This can be achieved by using interference bandpass filters, with each of separate cameras 27 and 29. Any 3 filter sets can be used; usually, red, green and blue filters are used for the 3 color cameras.

The following linescan cameras are preferably used: 1×1024 element (high resolution), time delay integrated (TDI) CCD camera for size, shape and one color for camera 29, and 2×256 element (medium resolution) CCD camera for the other two colors, cameras 27.

A beamsplitter/filter combination allows all three cameras to see the same view simultaneously. Each camera has its own color filter, focusing lens and iris diaphragm. The magnification in the high resolution channel may be four times larger than in the other two channels.

The tablets in each stream pair are illuminated by two light strips from optical fiber light guides symmetrically disposed on each side of the vertical. This arrangement give maximum intensity of illumination on the tablets while minimizing illumination of the belt. Each pair of guides can be powered by a single electronically controllable light source.

The image acquisition is matched to the belt speed by using an encoder associated with the conveyor 23.

Image processing algorithms are model based with separate shape, size, and color models. Each model is learned automatically at the start of a batch as part of a TEACH procedure to be described hereinafter. This flexible approach allows all new tablet types to be taught with no operator programming required.

Tablet size, shape and color are determined as follows:

Tablet area measured by counting the number of pixels in each tablet candidate.

Tablet shape is measured by an R-theta algorithm. This works by first calculating the first area centroid of the tablet and then measuring the radius of the tablet relative to the center at a number of equal angular increments. A shape template of the tablet as radius versus angle in degrees is stored in the system. An observed object (tablet) is correlated against the template and its matching error calculated. The shape test is a 2 stage process:

(1) check for a high correlation between the template and the object's R-theta profiles (2) check for a low matching error between the correlated profiles The color test involves looking at the color difference between the tablet and a color model learned at start of each batch by averaging over a statistically significant number of tablets during the TEACH procedure.

The color model is both the direction (hue) and the magnitude (brightness) of the color vector in "RGB" space.

The color measurements involves averaging the brightness level of the pixels in the 3 color channels to give a single number in each channel, so processing is straightforward. Brightness limits are used to exclude highlights and shadows. This is because color measurement is inaccurate in dark and highlighted regions.

Rogue tablets can be detected by color differences, since tablets having the same shape but different colors are packaged. If a rogue tablet was detected then this might stop the line. The system configuration does not detect a rogue tablet (as opposed to a reject tablet) by size or shape as the object could be a broken tablet, but modifications to the software are possible, and the system is not limited to this configuration.

The image processing electronics hardware 31 is preferably a single printed circuit board integrated with the cameras and optics in a single module for each feeder channel 21. The cameras and optical components can be pre-aligned on a jig. The modules are interchangeable and no set-up is required. A jig can then be supplied when setting up the system on site. Each inspection system module can have its own power supply and light source.

The inspection system operates under the control of, and outputs its decisions to the diverter control 25. The decision for each tablet can be:

accept reject recycle rogue

Each inspection system 3 interacts with a tablet diverter system 5 to divert each tablet based upon the decisions rendered for each tablet inspection.

Tablet Diverter System

With reference again to FIG. 1, the tablet diverter system 5 is provided for each of the pairs of tablet streams 21 leaving the conveyor system 23 and inspection system 3. The tablet diverter system 5 includes a first tablet diverter step I identified by the reference numeral 35 which diverts the tablet based on a signal from the diverter control 25 to a recycle stream 37, reject stream 39 or accept stream 41.

A second diversion is performed designated by the reference numeral 43 wherein each tablet is diverted to a bottle "A" stream 45 or bottle "B" stream 47.

The streams 45 and 47 representing the pair of streams from the conveyor system 23 are combined by a chute 49 to produce a single feed 51 or 53 to the bottle conveyor system 7. Optical passage sensors 55 are provided to detect each stream of tablets 45 or 47 for each tablet diversion step as described below. These optical passage sensors provide tablet count verification. The primary tablet counting is done from the inspection system results and these additional sensors verify that the tablets have been correctly sorted by the diverter mechanism. Any unanticipated objects seen by these sensors will be treated as an error, and the bottle rejected.

With reference again to FIG. 2, in a preferred embodiment, the tablet diverter system 5 comprises a diverter body 57 which receives the tablets 59 in free fall off the end of the conveyor 61. Although the diverter body 57 has two sets of chutes, one for each of the two tablet streams 21, only one stream of tablets and one chute are shown in FIG. 2. The diverter body 57 provides a free fall path such that the tablets 59 do not touch the sidewalls until they have been diverted.

Each chute has three mechanical flaps 63, 65 and 67, respectively, to divert the tablets 59 into the correct chute. No tablets are diverted more than once. The flaps can be mounted on shafts with keyed ends which engage with rotary pneumatic actuators 69 for flap operation. The diverter body and flaps can be easily removed in the overall system for cleaning.

In operation, the pneumatically actuated mechanical flaps divert the tablets into the correct chute. This is done by the diverter control 25, whose primary function is to count and route tablets to their correct destination on the basis of the result of inspection. The diverter control sorts the tablets on the basis of two decisions.

The first decision determines whether the tablet is good, should be rejected or should be recycled, i.e., tablet diverter step I in FIG. 1. If rejection or recycling is required, the diverter is positioned accordingly. That is, with reference to FIG. 2, flap 63 is positioned as shown in cross hatch to divert the tablet 59 to the recycle stream. Likewise, flap 65 can divert the tablet to the reject stream if necessary. If the tablet is good, it is necessary to perform a second decision, diverter step II in FIG. 1.

The second decision checks the availability of bottles to be filled. Once a bottle has been filled, i.e. bottle "A", and is detected in the bottle conveyor system 7, the flap 67 is switched over and the bottle "B" can be filled, providing that a bottle is available. As will be described hereinafter, the full bottle is pushed out of a bottle escapement mechanism of the bottle conveyor system so that an empty bottle can be placed in the filling system. If no bottles are available, tablets on the conveyor are recycled and an error message can be reported to the filling station control 9.

Tablets going into the reject 39 or recycle 37 streams are checked indirectly by checking whether the diverter flap position is in the correct position and no foreign tablets are seen to enter the bottles.

Depending on the diversion of flap 67 into bottle "A" or bottle "B", the two tablet stream is combined using a static funnel piece for feeding into the bottle.

The recycle stream 37 can be directed to a collection bin or back to the tablet hopper 11, see FIG. 1. The rejected tablets can also be directed to a collection bin for proper disposal.

Figure 8:
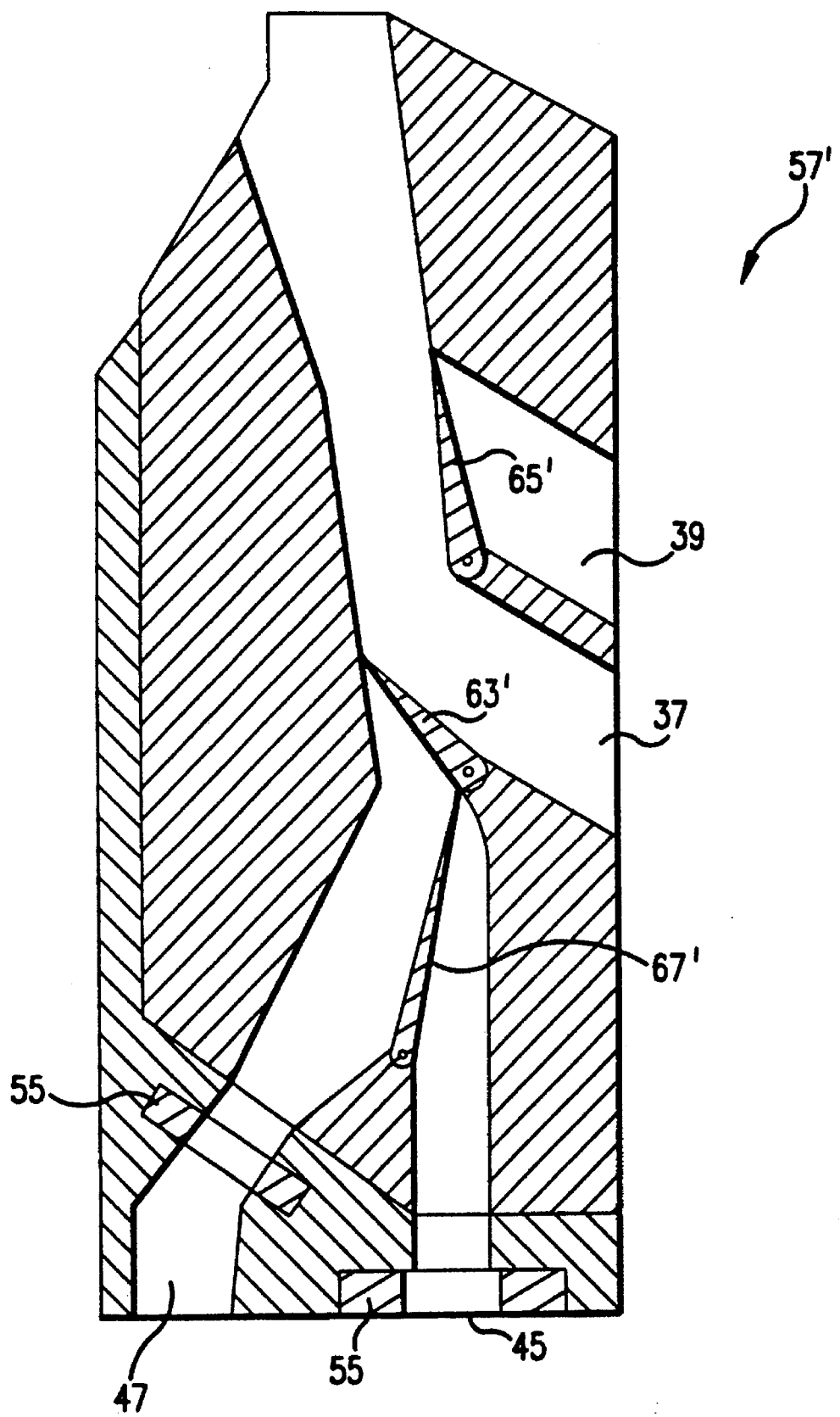
FIG. 8 is a cross-sectional view of an exemplary tablet diverter.

With reference to FIG. 8, a preferred tablet diverter body is generally designated by the reference numeral 57' and includes flaps 63', 65' and 67'. Flap 63', shown in the operative position directs the tablets into recycle line 37. Flap 65', shown in the inoperative position, controls flow of tablets into the reject line 39.

Flap 67' controls tablet flow between bottle "A" stream 45 and bottle "B" stream 47. Optical passage or count verification sensors 55 are provided in each stream 45 and 47.

The tablets flowing into either stream 45 or 47 are then combined with a parallel stream in diverter body 57' via a chute (not shown) for bottle filling.

Bottle Conveyor System

With reference back to FIG. 1, the bottle conveyor system 7 comprises a bottle source 71 which feeds bottles to the in-feed bottle conveyor 73. The in-feed bottle conveyor transfers the empty bottles to the bottle escapement mechanism 75. This mechanism is adapted to position an empty bottle to receive tablets from either of streams 51 or 53.

Once a bottle is filled, the filled bottle is removed from the bottle escapement mechanism 75 by an out-feed bottle conveyor 79. Incorrectly filled bottles can be diverted by the bottle diverter 81 based upon a discrepancy between the diverter control 25 and the tablet count generated by the optical passage sensors 55. The bottle diverter 81 can divert the incorrectly filled bottle to a rejected bottle stream 83. Correctly filled bottles can pass through into the filled bottle stream 85.

Figure 3:
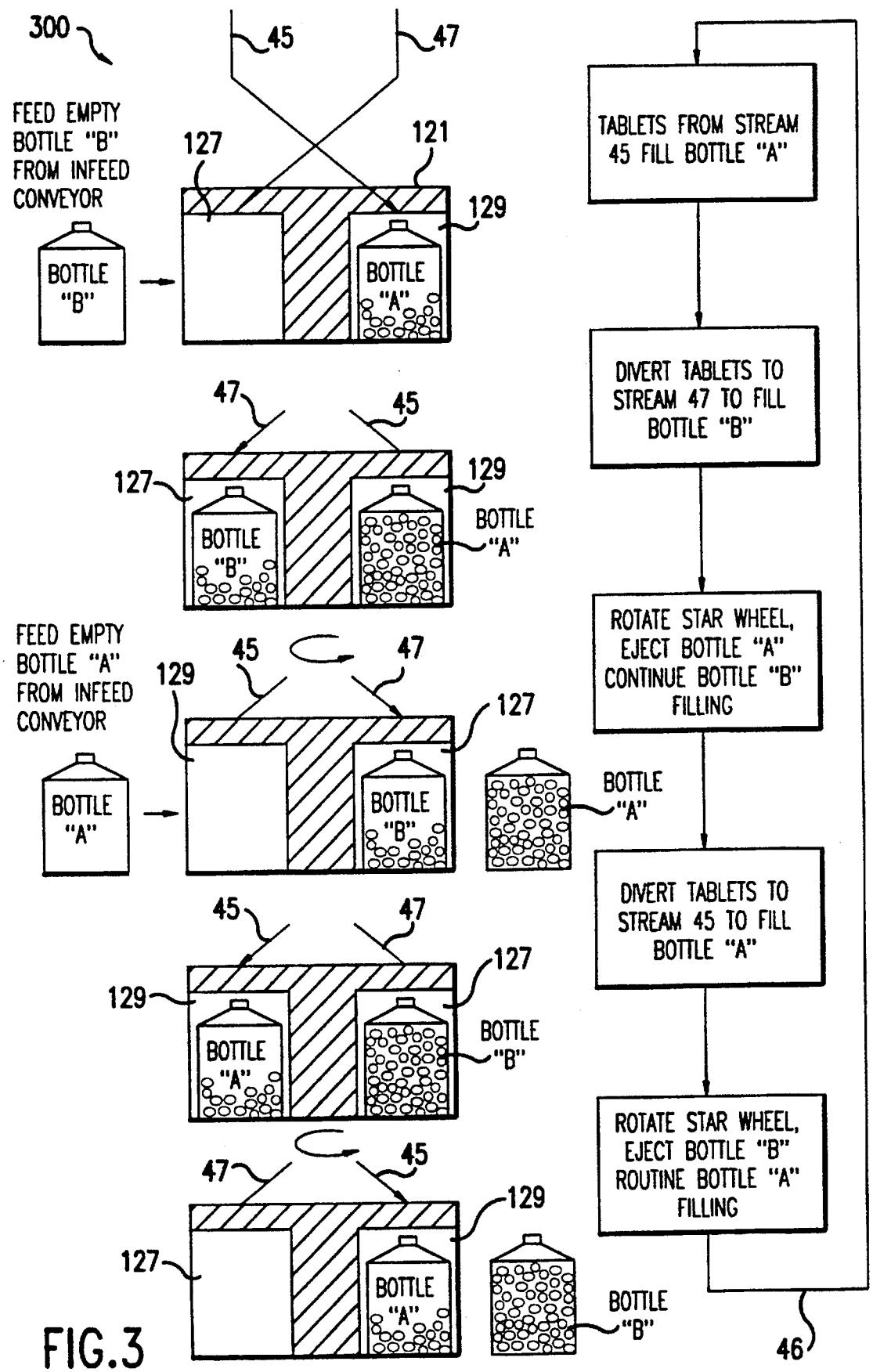
FIG. 3 is a schematic representation of the bottle filling system of the invention.

In a preferred embodiment, with reference to FIG. 3, the bottle conveyor system 7 can include the following:

A 3 meter long, in-feed conveyor. The in-feed conveyor system itself comprises of:

a 4½" wide main in-feed slat chain conveyor a 3¼" wide recirculating slat chain conveyor Bottles can be deposited, standing upright, onto the main in-feed conveyor which takes bottles to a bottle escapement device under each diverter channel. If all the bottle escapement devices have bottles present, then bottles on the main in-feed conveyor that have passed all the escapement devices will be transferred onto the recirculating conveyor designated as recycle 74 in FIG. 1, and thence return upstream onto the main in-feed conveyor once again.

Each tablet diverter 5 has its own separate bottle escapement mechanism 75—a simple interchangeable star wheel with two positions at 180 degrees. These correspond to the two bottle filling positions 51 or 53 for streams 45 and 47, respectively.

Figure 9:
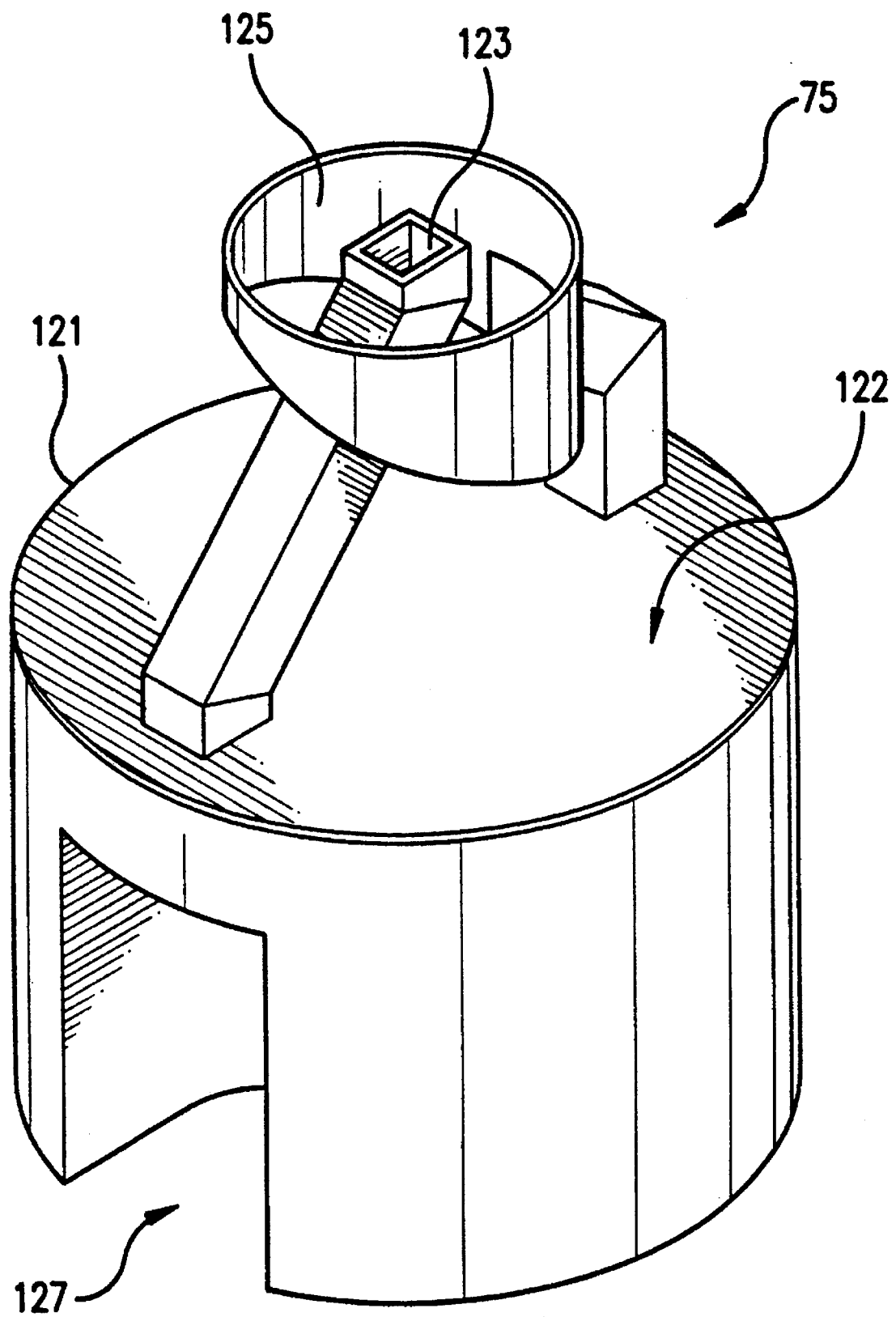
FIG. 9 is a front perspective view of a container filling device.
Figure 10:
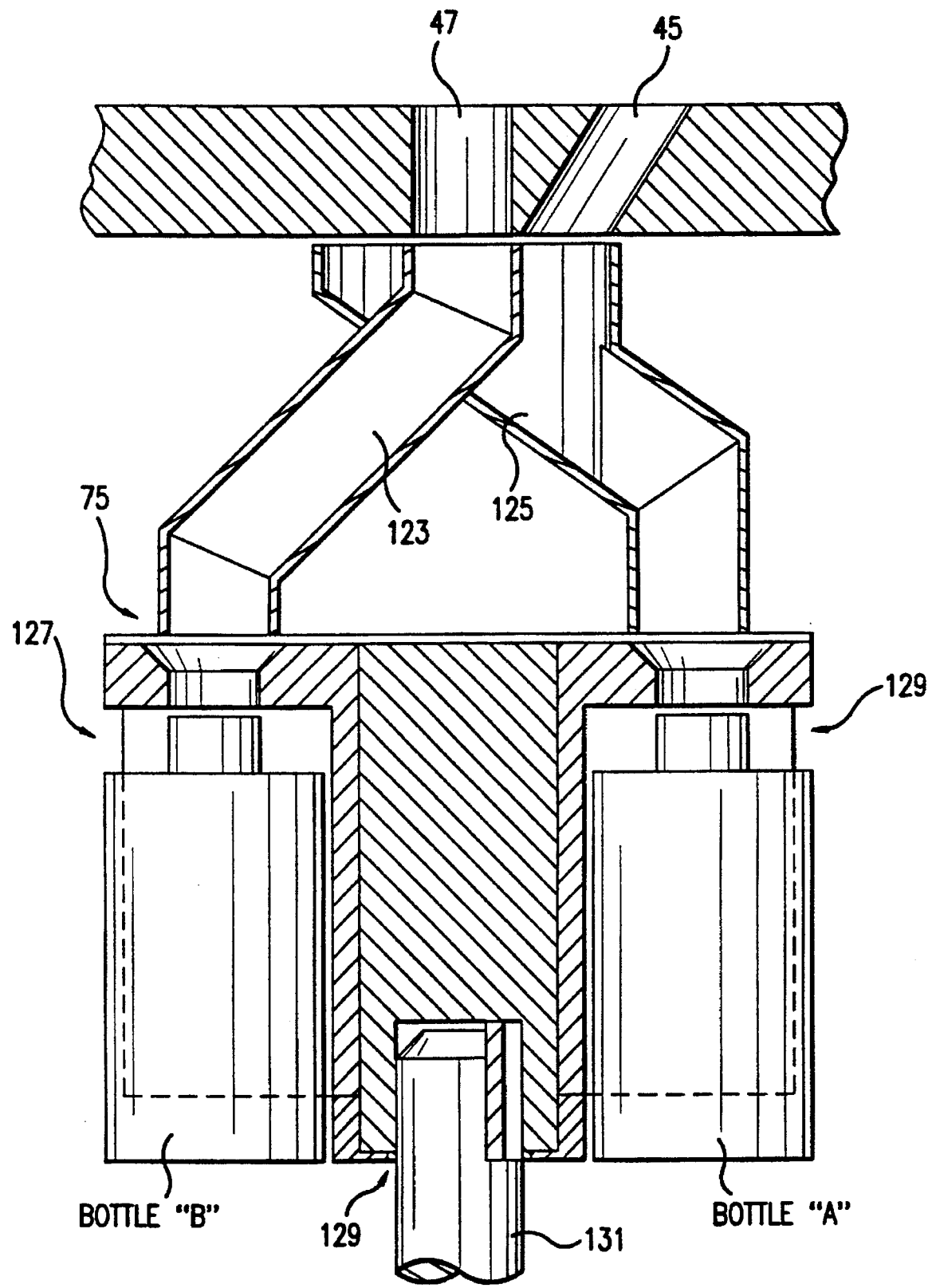
FIG. 10 is a cross-sectional view of the filling device of FIG. 9.

With reference to FIGS. 9 and 10, the bottle escapement mechanism 75 includes a starwheel body 121. Extending from the surface 122 of the body 121 are a pair of chute structures 123 and 125. As can be seen from FIG. 10, chute structure 123 provides communication between bottle B stream 47 and bottle B situated in the bottle filling station or recess 127. In a similar manner, chute structure 125 provides communication between bottle A stream 45 and bottle A, located in bottle filling station 129.

The starwheel body 121 has a bore 128 which receives a spindle 131 of a drive mechanism (not shown) to rotate the starwheel as will be described hereinbelow.

The motion of the star wheels is intermittent—the star wheel rotates by 180 degrees when a bottle has been filled, this motion feeds the filled bottle out onto the bottle out-feed conveyor traveling beneath the station. While the star wheel is rotating, the other bottle is being filled.

In operation, the diverter valve 67 or 67' is positioned such that the tablets accepted in the tablet converter mechanism 5 are introduced into bottle A stream 45. During filling, bottle filling station 129 is positioned adjacent the outfeed bottle conveyor 79. Thus, when bottle A is filled, the starwheel is rotated by 180°, this rotation driving filled bottle A along the outfeed bottle conveyor 79, see FIG. 1.

At the same time, once bottle A is filled, the diverter flap 67 or 67' moves to divert the flowing stream of tablets into bottle B stream 47. These tablets are directed into chute structure 123 of the starwheel body 121 to fill bottle B positioned in bottle filling station 127. It should be understood that once bottle A has been filled and the starwheel rotates to discharge bottle A into the outfeed bottle conveyor 79, bottle B is rotated in the starwheel 180° while it is being filled with tablets.

During rotation of bottle B in the starwheel, the bottle filling station 129, now empty, is positioned adjacent the bottle infeed or the infeed bottle conveyor 73 to accept an empty bottle. By this arrangement, either bottle A or bottle B is receiving the continuous flow of tablets through either chute structure 123 or 125. Thus, there is no interruption in tablet feeding and the high rate of bottle filling can be achieved.

When bottle A is being filled in bottle filling station 129, there is ample time during the filling cycle for an empty bottle on the infeed bottle conveyor to be directed by a diverting flap or the like in the infeed bottle conveyor stream to fill the bottle filling station 127 before the rotation of the starwheel body 121.

For example, the star wheel will take approximately one second to rotate, thus for a 100 tablets/bottle fill level, the star wheel will be stationary for approximately 7 seconds. This provides ample time for another empty bottle to be fed into the empty filling station 129 from the bottle in-feed conveyor.

The drive mechanism for each star wheel is a pneumatic semi-rotary actuator coupled to a single way indexing unit. A stop cylinder ensures 180 degrees movement. Sensors detect the position of the escapement mechanism and bottles at the in-feed position.

Incorrectly filled bottles (as detected by a discrepancy between the diverter control and the diverter chute sensors) are diverted automatically on the bottle out-feed conveyor into a holding area or pen.

With reference to FIG. 3, a representative cycle of the bottle escapement mechanism sequencing is generally designated by the reference numeral 300 and shows a first step of bottle A being filled with tablets from stream 45 exiting the tablet diverter (not shown). The starwheel 121 is shown with an empty station 127. An empty bottle B is fed into station 127 from the infeed conveyor.

Once bottle A is filled, tablets are diverted to stream 47 to fill bottle B.

The starwheel is then rotated to eject bottle A while continuing to fill bottle B in station 127.

Another empty bottle designated as bottle A is then fed into the empty station 129 from the bottle infeed conveyor.

After bottle B has been filled, tablets are diverted to stream 45 to fill bottle A.

The starwheel is rotated again to eject bottle B along the outfeed bottle conveyor while continuing to fill bottle A during rotation thereof. The bottle filling sequence begins another cycle as represented by the recycle line 46 in FIG. 3.

Figure 11:
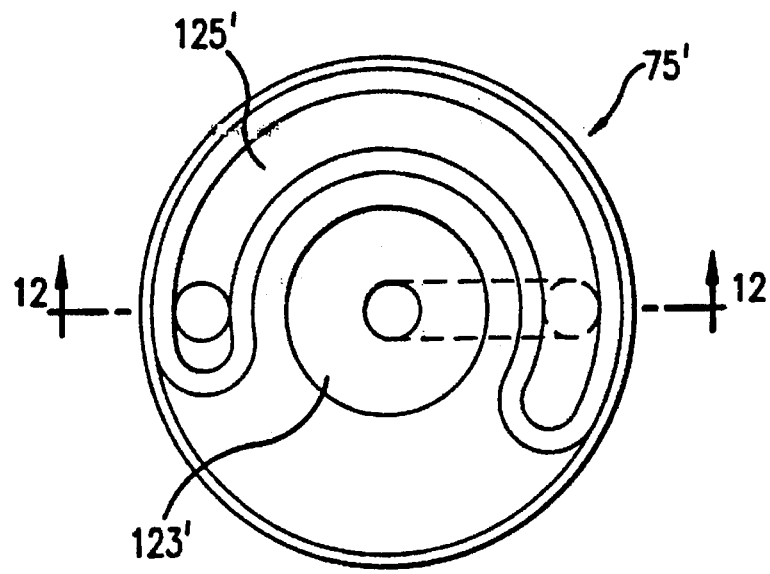
FIG. 11 is a top view of another embodiment of the container filling device.
Figure 12:
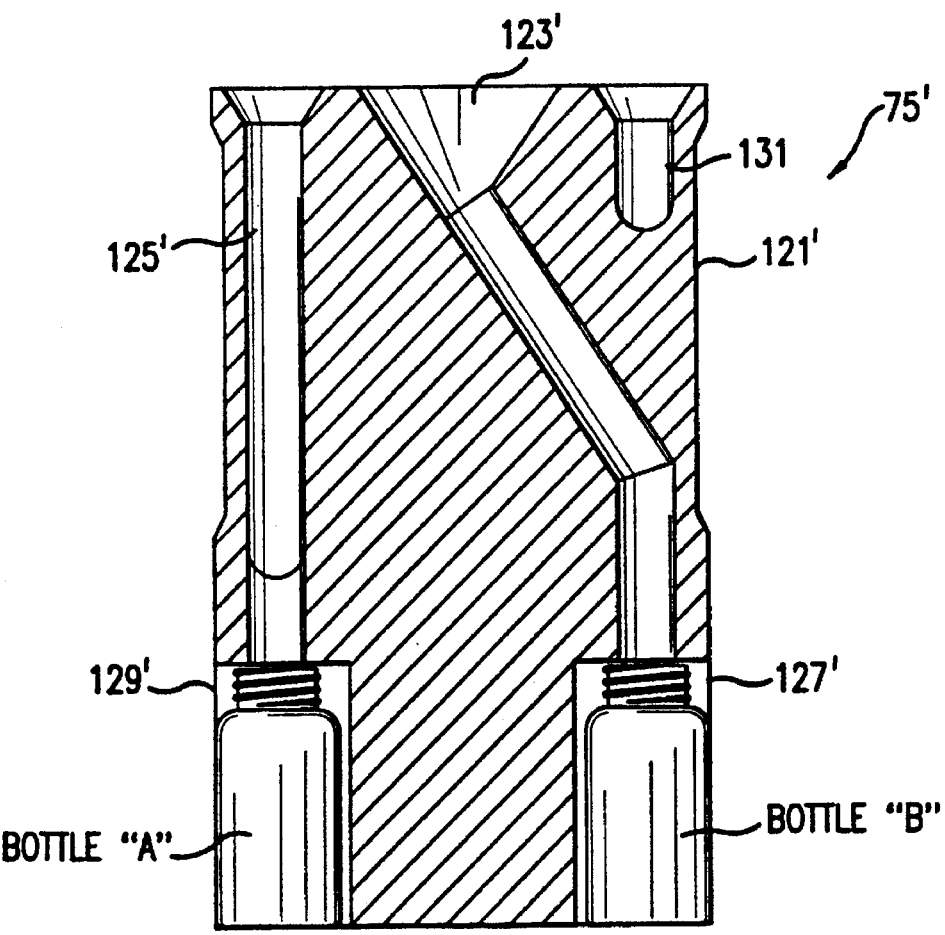
FIG. 12 is a cross-sectional view along the line x-x of FIG. 11.

With reference to FIGS. 11 and 12, an alternative bottle escape mechanism 75' is shown. In this embodiment, the starwheel body 121 has the chutes 123' and 125' formed therein rather than separate structures extending from an upper surface of the starwheel body as shown in FIGS. 9 and 10. In this embodiment, chute 125' has a trough 131 which extends part way around the circumference of the body to permit continual filling of the bottle position there below during starwheel body rotation.

In the embodiment shown in FIGS. 11 and 12, the bottle B would then be ejected into the bottle outfeed conveyor after being filled upon rotation of the starwheel body 121'. During this rotation, bottle A in bottle filling station 129' would simultaneously rotate and begin to be filled by tablets diverted into chute 125'. Empty bottle filling station 127' would then receive another empty bottle from the bottle infeed conveyor 73 to continue the bottle filling cycle.

It should be understood that the bottle escapement mechanism can be utilized for the continuous filling of continuous stream of traveling empty bottles in any application involving a continuous stream of traveling articles. For example, vitamins or candies could be diverted between the starwheel chutes and to fill containers positioned in the starwheel body openings or recesses.

Control System

The inventive system and method has a distributed control system. That is, the system is designed to optimize data flow between the distributed control elements. With reference to FIG. 1, a controlling supervisor computer, preferably an IBM type PC 386 functions as the filling station control 9 which communicates via serial interfaces with a number of custom interface boards, each with its own CPU. The custom interface boards correspond to the tablet conveyor system control 19, the diverter control 25 and a bottle conveyor system control 87.

The filling station control 9 provides an operator terminal including a video display unit 89 displaying information pertinent to filling station operations and an operator input 91 in the form of a keyboard. The filling station control performs primary control functions as follows:

receives commands from the operator keyboard;

displays information on the screen;

coordinates the distributed controllers;

responds to detected error conditions; and processes and stores data.

It should be understood that the diverter control 25, the bottle conveyor system 87 and the tablet conveyor system control 19 are shown in FIG. 1 controlling the overall tablet system, the bottle conveyor system and tablet conveyor system, respectively, identified in rectangular cross hatch.

Figure 4:
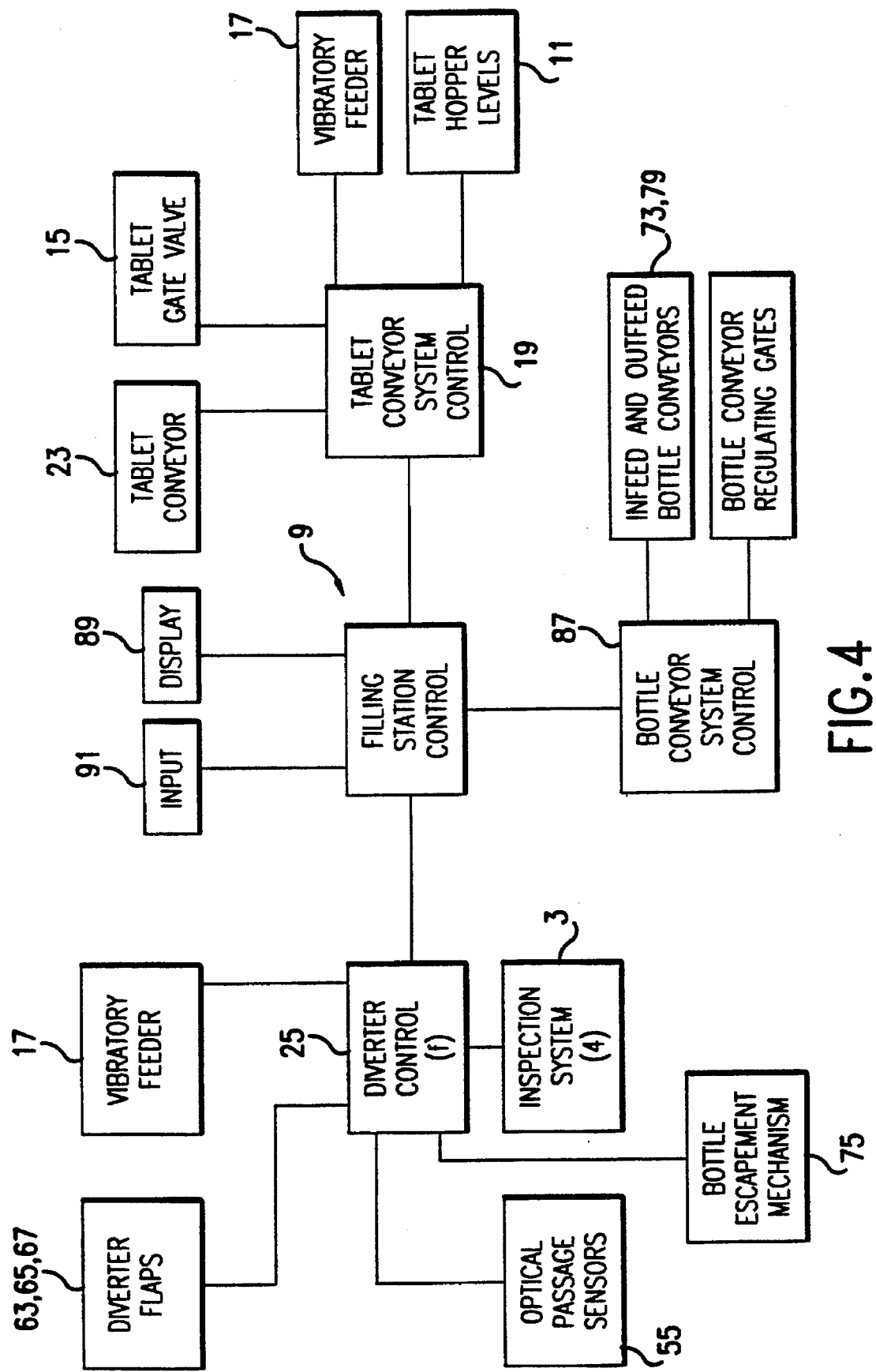
FIG. 4 is a schematic diagram depicting the general architecture of the filling station control system.

FIG. 4 shows a more detailed schematic of the control system for the inventive system and apparatus. The diverter control 25 controls analog and digital inputs and outputs associated with the diverter flaps 63, 65 and 67, the bottle escapement mechanisms 75, the vibratory feeder 17, the optical passage sensors 55 and each of the inspection systems 3 monitoring the pair of tablet streams 21.

The filling station control 9 also communicates with the tablet conveyor system control for control of the tablet conveyor 23, the hopper gate valve 15, the amplitude of the vibratory feeder 17 and tablet hopper levels monitored by sensors therein. This control also indicates to the filling station control when tablet replenishment is necessary.

Finally, the bottle conveyor control 87 controls input and output associated with the filling station as a whole, in particular, the bottle feed conveyors 73 and 79 and their regulating gates 78. The system can be shut down by a human operator if the bottles jams. The regulating gates 78 can be any type gate or diverter that direct bottles into or out of the bottle escapement mechanism, e.g. a flap or plate extending into the conveyor to catch direct bottles to a filling station. Alternatively, the bottle conveyors can be positioned below the filling station to feed bottles thereto or facilitate bottle exiting therefrom.

For each filling system, there is one inspection system, one diverter mechanism and one bottle escapement mechanism for each pair of tablet streams 21. Given that there are four pairs of tablet streams, there are four total inspection systems, tablet diverter systems and bottle escapement mechanisms. This is represented in FIG. 1 wherein only a single pair of tablets streams 21 is depicted passing through the inspection system 3, tablet diverter system 5 and bottle escapement mechanism 75. A single table conveyor system control 19 and bottle conveyor system control 87 are provided with the bottle filling system.

Figure 5:
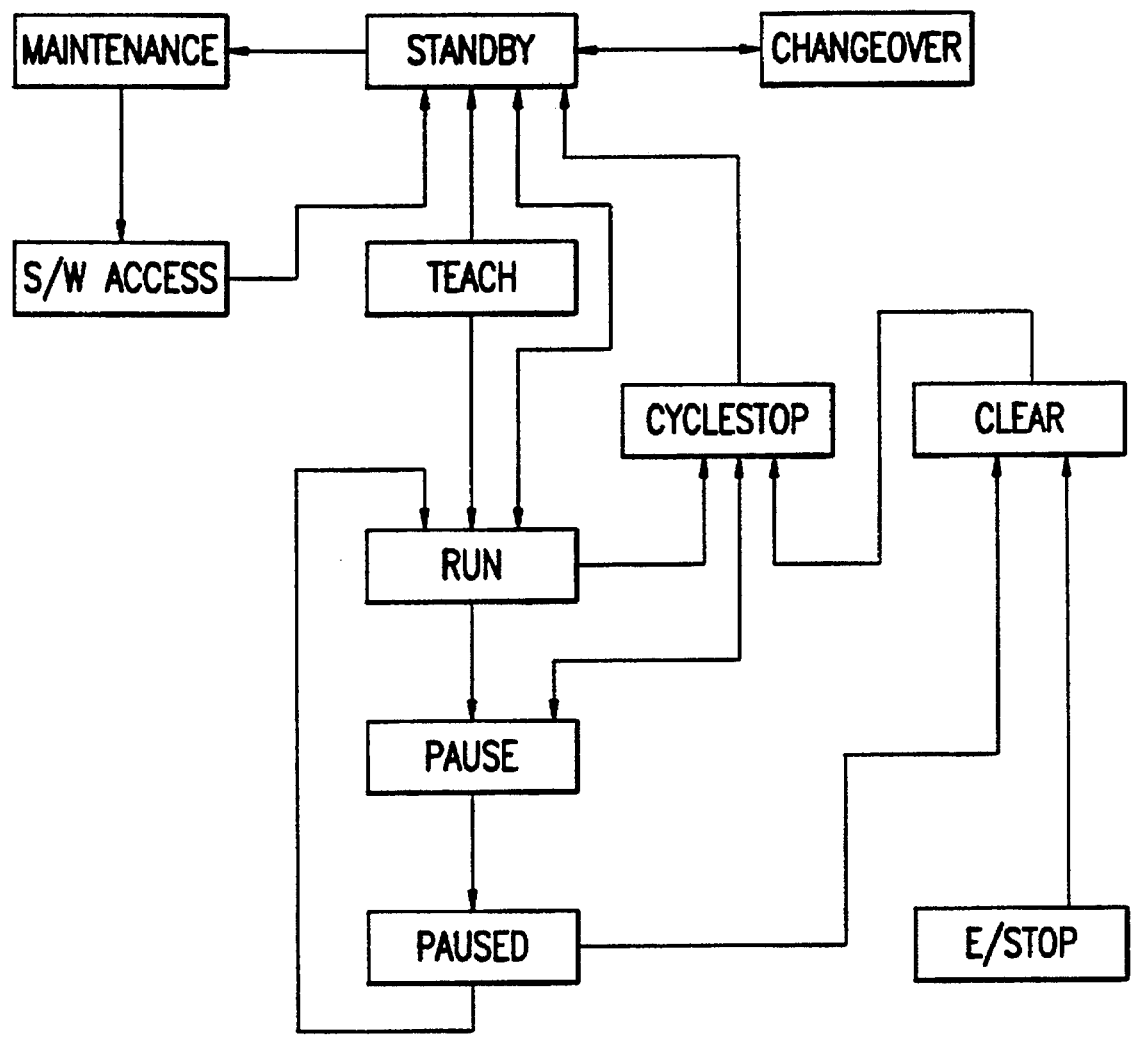
FIG. 5 is a schematic diagram showing the operating states of one of the control systems of the invention.

While the filling station control can be designed in any known fashion to totally automate the system 10, it may operate in the states shown in FIG. 5. Much of these states represent a certain operating state for the overall system.

For example, the maintenance level allows a maintenance technician to calibrate the inspection system. S/W Access (software access) permits programming changes to be made by an authorized user.

In the standby mode, all moving parts of the machine are stationary and bottles in the bottle escapement outlets are empty.

The changeover state is designed to lead the operator through a line strip-down procedure, new batch of tablet data entry and line set-up. Line strip-down entails emptying the various hoppers and bins associated with the system and removing and/or cleaning components prior to start up. The new batch tablet data entry permits an operate to specify the operating parameters such as batch quantity, bottles per minute, product strength, nominal tablet size, expiration date and PSF code for a system ran. The line set-up procedure involves installation of the components removed for cleaning so that the system is ready for operation.

In the teach state, the system will learn the tablet model for the current tablet to be processed. This state will be discussed in more detail hereinbelow in conjunction with discussion of the inspection system operation.

In the pause state, the system may be temporarily stopped by detection of an error as discussed below.

In the paused state, production can be restarted by entering the mn state. Alternatively, the system will execute a cyclestep if the clear state is selected.

Finally, the emergency stop state, as discussed above, shuts down the entire system. Once the emergency stop loop is complete, the clear state can be entered to begin additional sequencing.

All states allow full page viewing of an event log described herein below.

The following Table identifies the states of the various components of the inventive system when in a given state.

TABLE I

| | Hopper Off | Vibratory State | Inspection Conveyor | Bottle Conveyor | Diverter State | IS State | Star Wheel |
|---|---|---|---|---|---|---|---|
| Standby | — | off | off | off | recycle | taught or not taught | empty |
| Changeover | — | off | off | off | recycle | taught or not taught | empty |
| Maintenance | — | — | — | — | — | — | — |
| Cal IS Gain | — | — | — | — | — | — | — |
| Cal IS Offset | — | — | — | — | — | — | — |
| Cal IS Position | — | — | — | — | — | — | — |
| Teach | open | on | on | — | recycle | teaching | empty |
| Run | open | on | on | on | operating | taught | occupied |
| Paused | — | off | off | off | recycle | taught | — |
| Cyclestop/Clear | open | on | on | on | operating | taught | occupied |
| Pause | open | off | on | on | recycle | — | — |
| E/Stop | — | off | off | off | recycle | — | — |

"IS" •Means inspection system; "IS taught" •Means all ISs taught; "IS not taught" •Means some ISs not taught; "—" •Means undefined; "CAL" •Means calibrate It should be understood that the calibration of the inspection system with regard to gain, offset and position will be discussed hereinbelow.

The filling station control also includes various error conditions to monitor system operation. Examples of such errors include out-feed conveyor backup, out-feed conveyor full, failure of an inspection camera, rogue tablet, wrong count of tablet, hopper low, inspection conveyor, or the like. Depending on the gravity of the error will determine whether merely a message is displayed on the operator terminal 89 to indicate that scheduled maintenance must occur or the system must be shut down to correct the error.

The control system will also be provided with an ASCII text file written and updated on an internal hard disk drive thereof for maintaining a history log of the system operation. The history log will include a tabulation of production including number of good bottles filled, bottles rejected, rate in bottles per minute, tablets rejected and tablets recycled.

The history log can also include an event log which monitors error messages, operating state changes, operator input and the like. Finally, the history log can also include a tablet model log which records the actual model data used in the inspection system when inspecting tablets.

With reference back to FIG. 2, the inspection system functions utilizing an interrupt service routine, interrupt service routine control code and core algorithms. Basically, the interrupt service routine receives the raw data from the line scan cameras 27 and 29 and associates it with objects which are then passed to the control code for validation. The control code manages the foreground which can operate in a number of modes, as well as communicating with the diverter control 25 by messages. When an object is passed to the control code from the interrupt service routine, the core algorithms are used to process and validate the object.

In an interrupt service routine, objects pass under the cameras on a belt in two streams. The camera hardware scans the streams on a line by line basis. On completion of the scanned line, the hardware generates an interrupt to the digital signal processor. In response to the interrupt, the digital signal processor reads a register which contains a count of the number of chords on the current line and reads the associated data from a first in first out buffer. This data contains the coordinates of the start of object chords and information on the color contained within the bounds of each of the chords.

The task of building each object from its chords is delegated to the core algorithms This process is known as object generation and includes the following: chord to object assignment, areas summation and color summation.

When a completed object is found by the interrupt service routine, it is passed to the foreground code for further processing. If the object is too small or too long, it is treated as an invalid object.

When an object is received by the foreground code, it is processed for color, size and shape. Depending on the outcome of this processing, a message is sent to the diverter control 25. The control code also communicates with the diverter control and controls the mode of operation of the inspection system.

The core algorithms are used by the control code for object validation. The core data supplied from the interrupt service routine is transformed into a boundary description and then finally into a radial description at uniform angles around the boundary. The color of the tablet is also calculated. Depending on the mode of operation, the resulting data is used for object learning, or compared against the stored reference for object validation. Given the description of the processing steps involved in the inspection system, generation of the necessary software is considered to be within the skill of the art.

When a line scan interrupt is generated by the hardware described above, it is serviced by the inspection system's interrupt service routine. That is, for each scanline, the following data is read:

For each line, a count of the number of chords on the current line; and

For each chord, the start and end position across the line of the chord, the sum of the red, green and blue components and the sum of area over which color information is obtained.

Each object description is first built up using the chords supplied by the camera hardware. The basic principle is that if two chords on adjacent scanlines overlap in the x direction, then they are chords of the same object. If a chord in a scanline cannot be matched to a chord on the previous scanline, it is the beginning of a new object; a new object in the object tablet is started. If no chord can be found on the current scanline for an object that is being built, then the object description is complete. Exceptions to these rules can occur for objects which have re-entrant boundaries to be discussed below.

Two chords overlap if at least one pixel location on the x axis is common to both chords. All chords which are connected together, or are connected via another chord, form pan of the same object.

Figure 6:
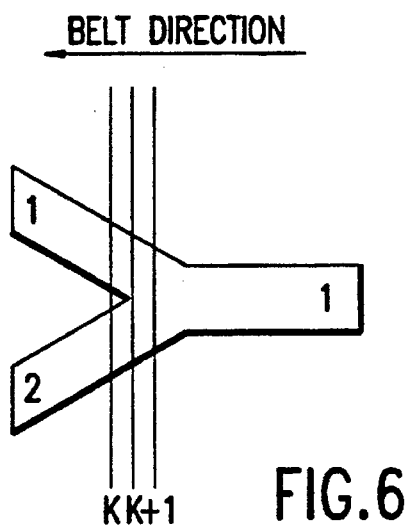
FIG. 6 is an example of a re-entrant boundary situation seen during inspection system.

A slightly complicated case is an object which has a re-entrant boundary. An example is shown by the sideways Y in FIG. 6. When the inspection system first sees chords from the object, it appears that the chords form two different objects. The chords are marked with object labels 1 and 2 (say) as shown in FIG. 6. At scanline k the object still appears to be two objects, but at scanline (k+1) the chord is connected to both of the current objects. The new chord is marked as being a chord of object 1, and the association variable of the object 2 in the object table is set to 1. All the subsequent chords in the object are marked as pan of object 1. The complete set of chords is gathered together by the foreground code.

For each object started by the interrupt service routine, the following statistics are gathered by the interrupt service routine and saved in an object table:

tablet area sum of red, green and blue color components object area over which valid color information was gathered length of object flags to indicate object has completed or too long associations between object because of re-entrance The interrupt service routine can also check for an inspection lamp failure by checking that there is always at least one chord, for the object diverter, on each scan line. If no chords are present on a line then a flag will be set to indicate lamp failure.

If the chord count for the line exceeds the number that can be processed between interrupts, then this indicates a data overload condition. When this condition is detected, a flag will be set to inform the foreground tasks.

The inspection system can be instructed to move between various operating states by receiving commands from the diverter control. While the inspection system is not returning data messages to the diverter control, a periodic status message shall be sent to the diverter control. The main inspection lamp will be dimmed in states that do not require the lamp.

On termination of all states, the inspection system will return to the Standby state.

The inspection system variables such as offset, gain and position can be calibrated as follows. The calibration state is used to perform calibration on parts of the optical system. It assumes that the correct user operation (placing of target under cameras, etc.) has been performed before calibration is invoked. Calibration should be performed in the correct sequence with offset done before gain. If an element of a camera gives readings which are outside expected limits, then it is assumed that this camera is defective and this information will be returned in the calibration end message. Any pixel filtering (lone pixel suppression) provided by the acquisition hardware must be disabled during calibration.

The purpose of offset calibration is to offset any output from the camera elements when no light enters the camera. The output from each element of the camera will be read from the framestore and averaged over several scan lines, the resultant value will be placed in the offset hardware and saved in non volatile memory.

The purpose of gain calibration is to normalize the output from the camera elements when light is entering the camera. This is used to compensate for variations in individual camera elements and inspection light intensity across the scan line. The output from the individual elements shall be averaged across several lines. These averages are then used to calculate the gain correction values to be written to the gain correction hardware, and saved in non volatile memory.

The purpose of position calibration is to put the vision hardware in a state to assist with camera alignment. This will include turning the inspection light up. The inspection system will stay in this state until commanded to leave.

The inspection system also performs the teach function to learn what parameters are to be monitored for a given tablet ran. In the teach state, the system will learn the tablet model for the current tablet. Teaching is done in two parts: finding a valid initial object to start the model, and then building the reference model starting from the initial object. To locate a valid initial object, teach will take a random start object and then try to match 2 other objects in the next 10 to within 5% for size and shape. If the match fails then teach will continue to take random start objects until a match is found. Once a valid initial object is found teach will match a larger number of objects (~25) for size, shape and color, and then add these to the model using a weighted averaging method if they match the model. The following information will be derived in the teach state:

R-theta profile for tablet area of tablet color vector and matching limits in RGB space highlight and black thresholds The Teach state will terminate when the model has been built from the correct number or objects of the inspection system is requested to exit teach mode. The teach state will only mn if the system has been successfully calibrated. During teach, all tablets should be recycled. Teach mode may not use every tablet to pass under the inspection system to build the model. On termination of a successful teach operation, the R-theta profile will be rotated so that the largest vector is in the first location of the tablet, and the model data sent to the filling station control.

In addition, the teach state checks against a master record for standards of the particular tablet being packaged, to avoid the machine calibrating itself against an incorrect sample.

In the run state, the inspection system monitors the pair of tablet streams based on taught parameters for bottle filling. During the run state, tablets are checked against the model obtained from the teach state. The result of the check and the timing information associated with a tablet are sent to the diverter control when the object has passed under the inspection system. For each object the timing information will consist of a time stamp for the leading edge (Ts) and the time from the trailing edge of the previous object (Tb). The types of objects that the inspection system expects to handle are described below.

Two streams of good objects For each of the objects the inspection system will send a message to the diverter control declaring the object as a valid object.

Objects whose area are too small Objects whose area is smaller than 2 mm will be ignored by the inspection system as too small, and therefore no message is sent to the diverter control for these.

Input overload If the number of transitions generated in a single scanline exceeds the number that can be processed between interrupts, or the number of active objects exceeds the size of the object table, then this indicates that the inspection system has overloaded with input data. This condition is an exception condition and is treated as such. The diverter control will be sent a recycle message and should recycle everything (both streams) until a valid object message is again received. The inspection system will empty the object table; the data acquisition first in and first out buffer is automatically cleared at the start of the next scanline.

Broken objects For objects which match for color but not for size or shape a reject message will be sent to the diverter control. The object image will be frozen in the framestore.

Rogue objects If an object does not match for color, a rogue object message is sent to the diverter control. The object image will be frozen in the framestore and the system will move to the standby state to wait for operator acknowledgement.

Overlapping objects For objects which overlap on a single stream a recycle message will be sent to the diverter control.

Objects that are too long Once an object has been detected as too long a recycle message will be sent to the diverter control.

During the life of the inspection bulb, its output spectrum will change (move towards the red end of the spectrum). While in the run state the system may need to adapt to this change in color by moving the acceptance criteria to track the color shift. If required this will be done by adjusting the acceptance color vector by an average of the mismatch in color detected for good objects.

During inspection, typically, the conveyor will be running at nominal speed of 200 mm/sec. Given a scanline width of 50 microns, this results in a four kHz (every 250 µs) linescan interrupt rate.

With the digital processor running a 50 ns cycle, it can execute 5,000 (250 µs/50 ns) instructions between interrupts. For the system to function, the digital signal processor must be able to read and pre-process all the data resulting from the line scan interrupt between interrupts, and on average, have enough time left over to process the completed objects in the foreground. Initial coding of the inspection system, and an assumption that on average 10 linescan pairs need to be read and processed at each interrupt, indicate that the inspection system will take less than 30% of the processor's time.

The largest tablet the inspection system is expected to handle is about 2 cm long. A tablet of this size will cover 400 scanlines (2 cm/50µ.). Assuming 10 transition pairs per scanline, three words of data per transition pair and two overlapping tablets in the field of vision, the main buffer needs to be 24,000 words long (400×10×3×2).

The maximum number of active objects in the system is assumed to 32 objects for each tablet stream. The threshold above which objects are deemed to be "too long" is typically 25 mm.

As described above, the inspection system will monitor up to 4 tablet streams and will direct the tablet diverter system via the diverter control to divert the tablets either to the recycle, reject, bottle "A" or bottle "B" streams. In addition, identification of a rogue tablet might stop the system.

Figure 7:
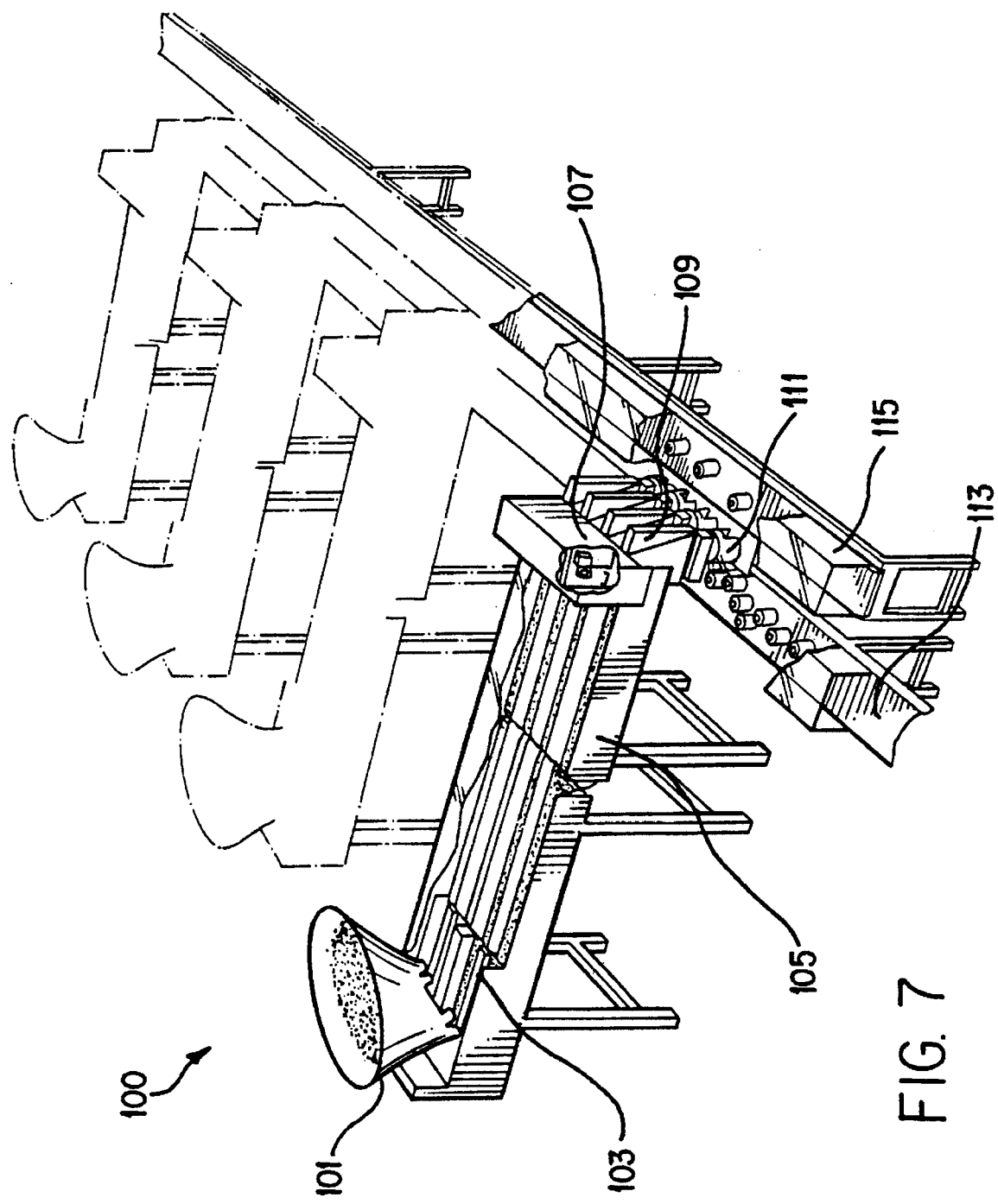
FIG. 7 is a perspective view of an exemplary modular arrangement of the inventive system.

With reference now to FIG. 7, a perspective view of an exemplary modular tablet filling system is designated by the reference numeral 100 and is seen to include a hopper 101, vibratory feeder 103, conveyor belt 105, tablet sensing module 107, tablet diverter 109, bottle escapement mechanism 111, bottle in-feed conveyor 113 and bottle outfeed conveyor 115. The bottle out-feed and in-feed conveyors 115 and 113 can service any number of systems. For example, FIG. 7 depicts four systems in total. As described above, each of the system components is easily removable and replaceable to facilitate cleaning and set up.

There is also a feedback loop from the tablet inspection system to the vibratory feeder 103, in order to increase or decrease the amplitude of the vibration to the tablet hopper 101 in order to increase or decrease the number of objects in each tablet stream.

By the inventive system, bottles can be automatically filled with a predetermined number and type of tablets which can then be directly distributed to the ultimate end user. The inventive system provides a high quality assurance operation that each bottle is filled correctly to ensure the safety of the end user.

As such, an invention has been disclosed in terms of preferred embodiments thereof which fulfill each and every one of the objects of the present invention as set forth hereinabove and provides a new and improved automatic system for the controlled filling of bottles with tablets.

Of course, various changes, modifications and alterations from the teachings of the present invention may be contemplated by those skilled in the art without departing from the intended spirit and scope thereof. Accordingly, it is intended that the present invention only be limited by the terms of the appended claims.

What is claimed is:

1. A device for filling individual containers in a moving stream of containers with a continuous stream of discrete items comprising:
   a) a body having:
      i) a first opening, a first recess sized to receive said container and a first chute interconnecting said first opening and said first recess;
      ii) a second opening, a second recess sized to receive said container and a second chute interconnecting said second opening and second recess; and
   b) means on said body for connecting said body to a drive that rotates said body in 180° segments;
   c) wherein said first recess and said second recess are located in said body on a line of said body intersecting a longitudinal axis thereof;
   d) wherein said first and second openings are sized and said first and second chutes are configured to receive said continuous stream of discrete items so that a container in either said first or said second recess can be continually filled with said discrete items traveling through respective said first or second chutes while said body is rotated said 180° segment.

2. The device of claim 1 further comprising a means for diverting flow of said continuous stream of discrete items between said first and second openings.

3. The device of claim 1 further comprising a device for rotating said body in said 180° segments.

4. The device of claim 1 wherein said first opening is aligned with said longitudinal axis of said body and said second opening surrounds said first opening and extends around a peripheral portion of said body.

5. The device of claim 1 further comprising means for delivering a continuous stream of tablets as said discrete items.

6. The device of claim 1 further comprising means for directing said individual container into an empty first or second recess.

7. The device of claim 1 wherein said body is cylindrical in shape, said first and second recesses are diametrically opposed on a side surface of said body and said first and second openings are located on one end of said cylindrical body.

\* \* \* \* \*